United States Patent [19]

Chen

[11] Patent Number: 5,778,880
[45] Date of Patent: Jul. 14, 1998

[54] HEART BEAT TRANSMITTER

[75] Inventor: Tong-Pie Chen, Taipei, Taiwan

[73] Assignee: Zentan Technology Co., Ltd., Taipei, Taiwan

[21] Appl. No.: 699,455

[22] Filed: Aug. 19, 1996

[51] Int. Cl.⁶ .............................. A61B 5/04; A61B 5/024
[52] U.S. Cl. ............................................ 128/696; 128/903
[58] Field of Search ........................ 128/696, 903, 128/706, 677

[56] References Cited

U.S. PATENT DOCUMENTS

| | | | |
|---|---|---|---|
| 4,952,928 | 8/1990 | Carroll et al. | 128/903 |
| 5,353,793 | 10/1994 | Bornn | 128/696 |
| 5,628,324 | 5/1997 | Sarbach | 128/903 |

FOREIGN PATENT DOCUMENTS 2257523  1/1993  United Kingdom ................ 128/903
WO88/09146  12/1988  WIPO ............................ 128/696

*Primary Examiner*—Marvin M. Lateef
*Assistant Examiner*—Carl H. Layno
*Attorney, Agent, or Firm*—Beveridge, DeGrandi, Weilacher & Young LLP

[57] ABSTRACT

An improvement of heart beat transmitter includes a circuit board, a pair of conductive rubber posts, a housing, a pair of fastening straps and a pair of conductive rubber plates. The housing is provided with a metal plate and installs the conductive rubber plate jointly with the fastening strap. The underside of the circuit board is provided with conductive spring plate or rubber post to establish a conducting loop with the metal plate to avoid the manufacturing difficulty. On the other hand, the conduction therebetween is enhanced. The conductive rubber plate is provided with an insulating layer to reduce the contacting area with skin. Accordingly, the noise interference is reduced and the performance is increased.

18 Claims, 7 Drawing Sheets

HEART BEAT TRANSMITTER

FIELD OF THE INVENTION

This invention relates to an improvement to a heart beat transmitter, more particularly, to the heart beat transmitter which can be used to monitor the heart beat for sport or medical applications.

The conventional heart beat transmitter comprises a housing, a transmitter situated in the housing, a female snap-fastener connected to the transmitter, a conductive rubber plate attached to a fastening strap by a male snap-fastener. When the male snap-fastener is engaged to the female snap-fastener, the conductive rubber detects the heartbeat when worn on the user's chest, and transmits detected cardiac signals to the transmitter and then to a receiver disposed on a watch or other device.

But the engagement structure between the male snap-fastener and the female snap-fastener is pretty complicated, causing increased manufacturing complexity. Furthermore, there is a gap provided for ensuring the engagement, and then there are two problems existed therein:
1. The gap will be the entrance of liquid, so as to damage the transmitter.
2. There is engagement shake, because of the gap, so as to cause noise and signal interference.

On the other hand, the heart beat transmitter is attached to the position of the user's chest wherein the conducting rubber plate is located at the central portion and extends to sides. This conducting rubber plate may generate signal when it detects the heart beat and transmits the resulted signal to the circuit board for decoding. Nevertheless, when a severe exercise is performed, since the contacting area of the conducting rubber plate is too large, it may detect different signals from different portions. This will no doubt cause an interference. On the other hand, the extension and retraction of chest muscle will also generate vibration, this will also effect the receiving of the heart beat.

SUMMARY OF THE INVENTION

It is the object of this invention to provide an improvement of heart beat transmitter wherein the heart beat signal can be accurately and steadily received in one hand, and the engagement between the fastener and buckle is improved to avoid penetration of liquid.

According to one preferred embodiment of the present invention, spring plates or conductive rubber posts are provided in the space between the circuit board and the metal plate to avoid the accurate tolerance required during the manufacturing. Furthermore, the electrical conductive connection is enhanced.

The present invention features the contacting area between conductive plate and skin is narrowed to reduce the interference thereof and enhance the detecting/receiving performance.

BRIEF DESCRIPTION OF DRAWINGS

The overall structure, means, features and its functions will become more apparent in conjunction with the following detailed description together with the drawings. A preferred embodiment according to this invention will be made for detailed description, wherein.

DETAILED DESCRIPTION OF THE PREFERRED EMBODIMENTS

Figure 1:
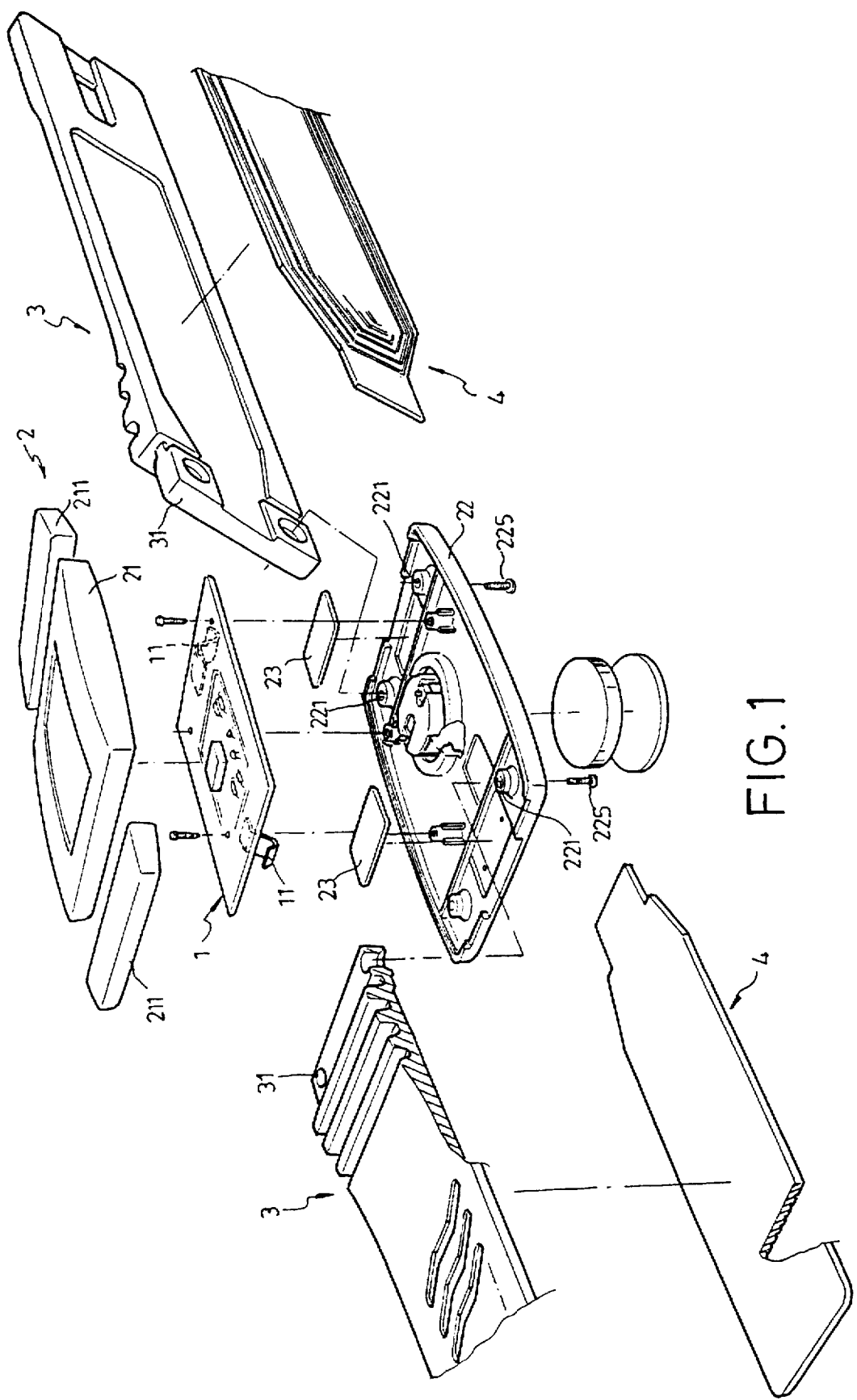
FIG. 1 is an exploded perspective view of the first embodiment made according to the present invention.
Figure 2:
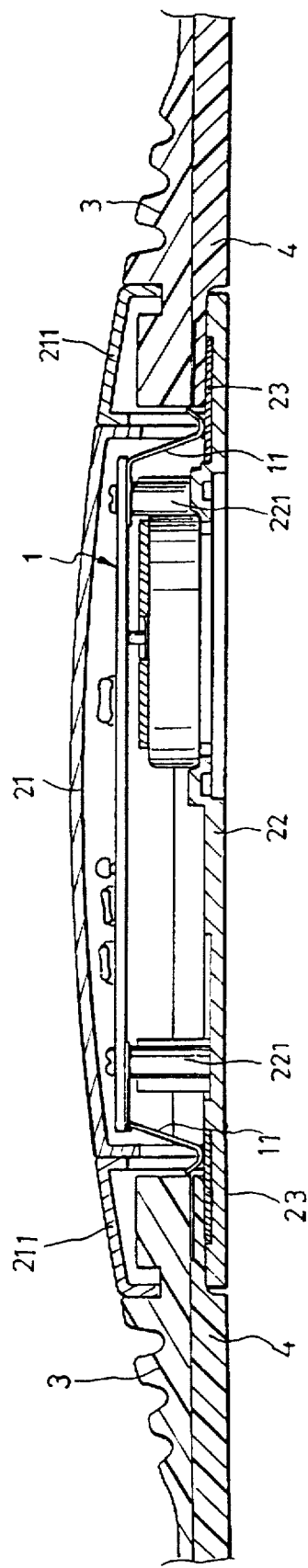
FIG. 2 is a cross sectional view of the heart beat transmitter shown in FIG. 1.

Referring to FIGS. 1 and 2, the heart beat transmitter made according to this invention includes a circuit board 1, a housing 2, a pair of fastening straps 3, and a pair of conductive plate 4. A transmitter is built in the circuit board 1 and is disposed within the housing 2. The housing 2 includes an upper case 21 which has a side cover 211 and an bottom case 22 which receives the upper case 21. Afterward, the fastening straps 3 are applied to fix the housing 2 onto the chest of user. Accordingly; the conductive rubber plate 4 is connected to the circuit board 1 to detect the heart beat of the user.

Characterized in that each of the side portions of the bottom case 22 of the housing 2 is provided with a metal plate 23 and the bottom case 22 is provided with boss 221 corresponding to said metal plate 23. The fastening strap 3 is provided with recessed portion for receiving the corresponding elongate conducting rubber plate 4. The fastening strap 3 is provided with a fastening portion 31 for engaging the boss 221 of the bottom case 22. On the other hand, the conductive rubber plate 4 is attached to the upper surface of the metal plate 23 of the housing 2. The underside of circuit board 1 is provided with a conductive spring plate 11 which is bent to a "√" shape (mathematical square root sign shape). The bottom of the spring plate 11 is biased to the upper surface of the metal plate 23 of the housing 2. By this arrangement, the spring plate 11 and conductive rubber plate 4 is electrically connected by said metal plate 23.

The first embodiment of the present invention can be concluded with the following advantages. Firstly, a metal plate 23 is disposed within the bottom case 22 and the conductive rubber plate 4 is attached to the fastening strap 3 corresponding to said metal plate 23. By the alignment of said elements, the uppercase 21 of the housing 2 and side cover 211 are attached to the bottom case 22. The upper case 21 and bottom case 22 are connected and welded ultrasonically, then a plurality of screws 225 are applied to fix the connection between the side cover 211 and bottom case 22. By this arrangement, all the elements are positioned within the housing 2.

Secondly, since the conductive spring plate 11 can move freely upward and downward, there is a robust distance between the conducting points between the circuit board 1 and the metal board 23. Accordingly, no special tolerance is required during the manufacturing. The assembly can be readily made without compromising the steady conducting performance.

Thirdly, the engagement between the upper case 21, bottom case 22 and the conductive rubber plate 4 are intact and tight, accordingly, no liquid may leak into the housing 2.

Figure 3:
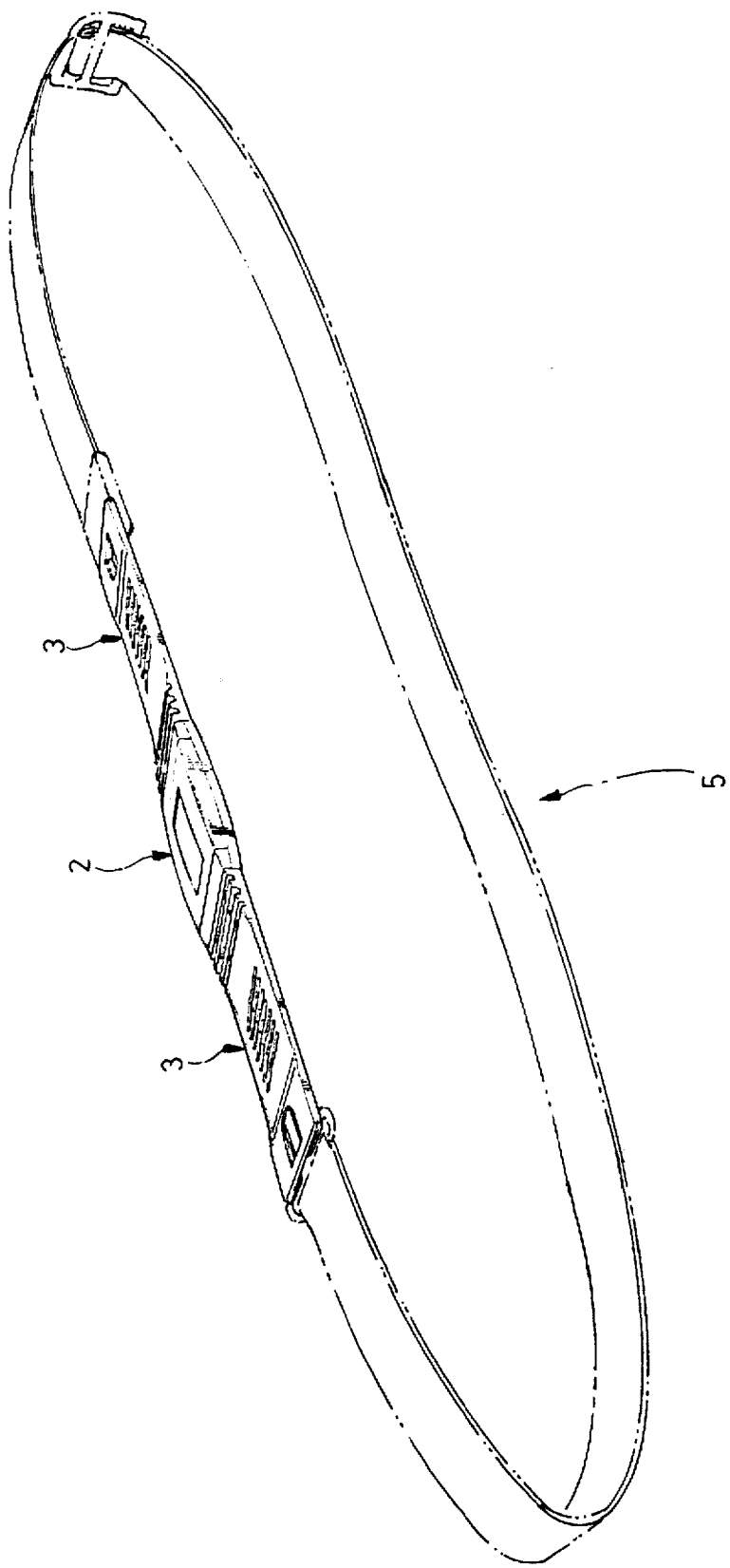
FIG. 3 is a sketch view showing the operation of the first embodiment.

The operation of this invention is with the strap 5, referring to FIG. 3. Both ends of fastening strap 3 are interconnected to the strap 5 and form a band together with housing 2 and fastening strap 3. On the other hand, the strap 5 can be adjusted to suitable length to fit the user's chest.

Figure 4:
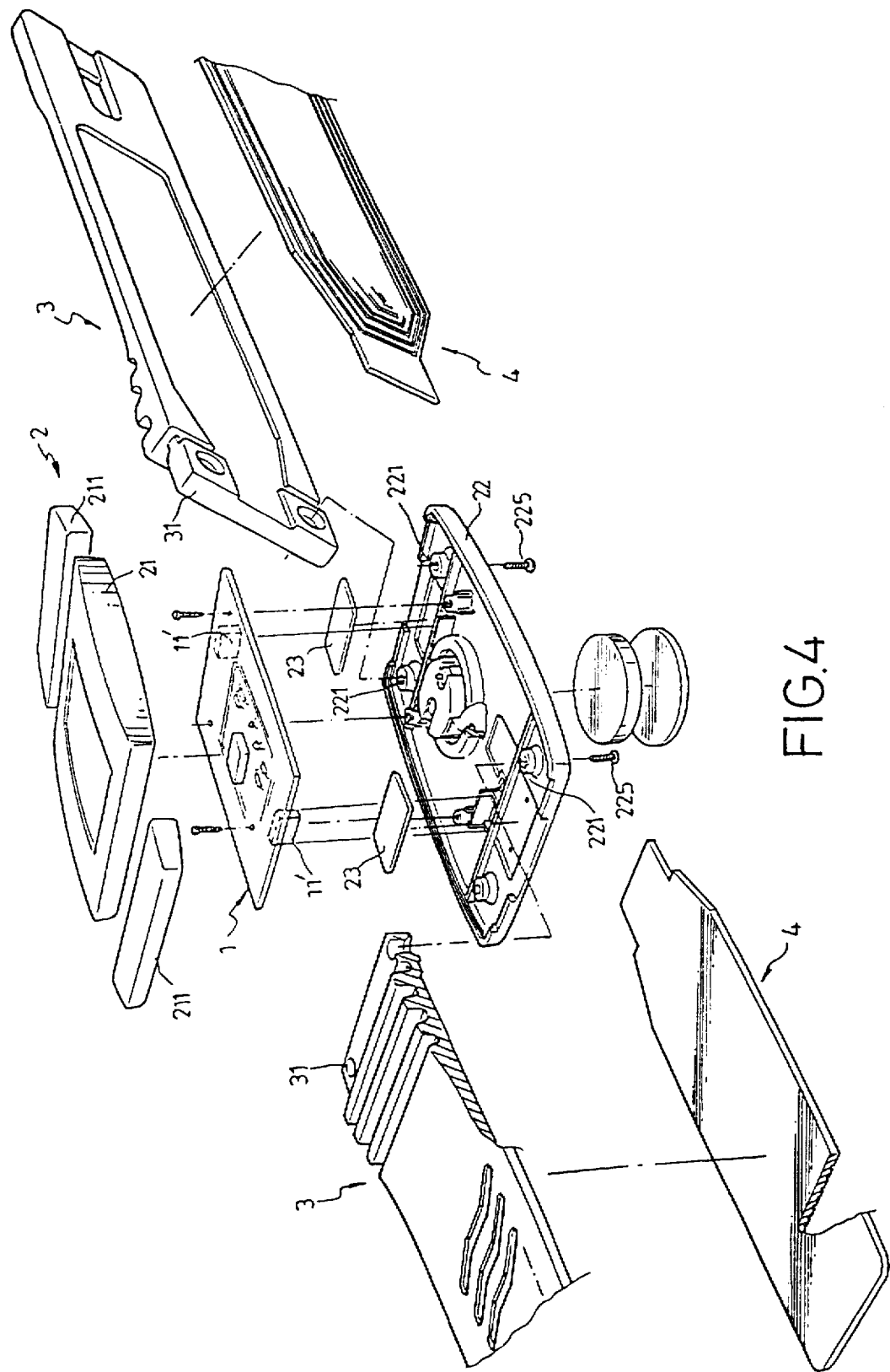
FIG. 4 is an exploded perspective view of the second embodiment made according to the present invention.
Figure 5:
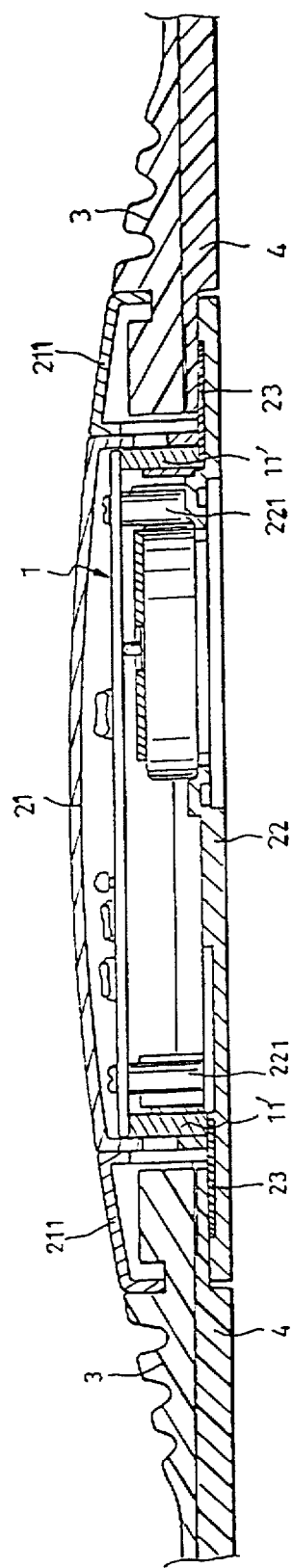
FIG. 5 is a cross sectional view of the heart beat transmitter shown in FIG. 4.

Refer to FIGS. 4 and 5 the second embodiment made according to this invention. In the space between the contacting points of the circuit board 1 and metal plate 23, a conductive rubber post 11' is provided. By this arrangement, the electrical conductive connection between the conductive rubber plate 4 and the circuit board 1 is made by metal plate 23 and the conductive rubber post 11'. Since the rubber post 11' has a robust elasticity it is readily retained between the metal plate 23 and circuit board 1. When the assembly is made, the electrical conductive connection can be readily made.

On the other hand, the conductive rubber post 11' can be replaced with conductive wires for the electrical connection between the circuit board 1 and the metal plate 23.

Figure 6:
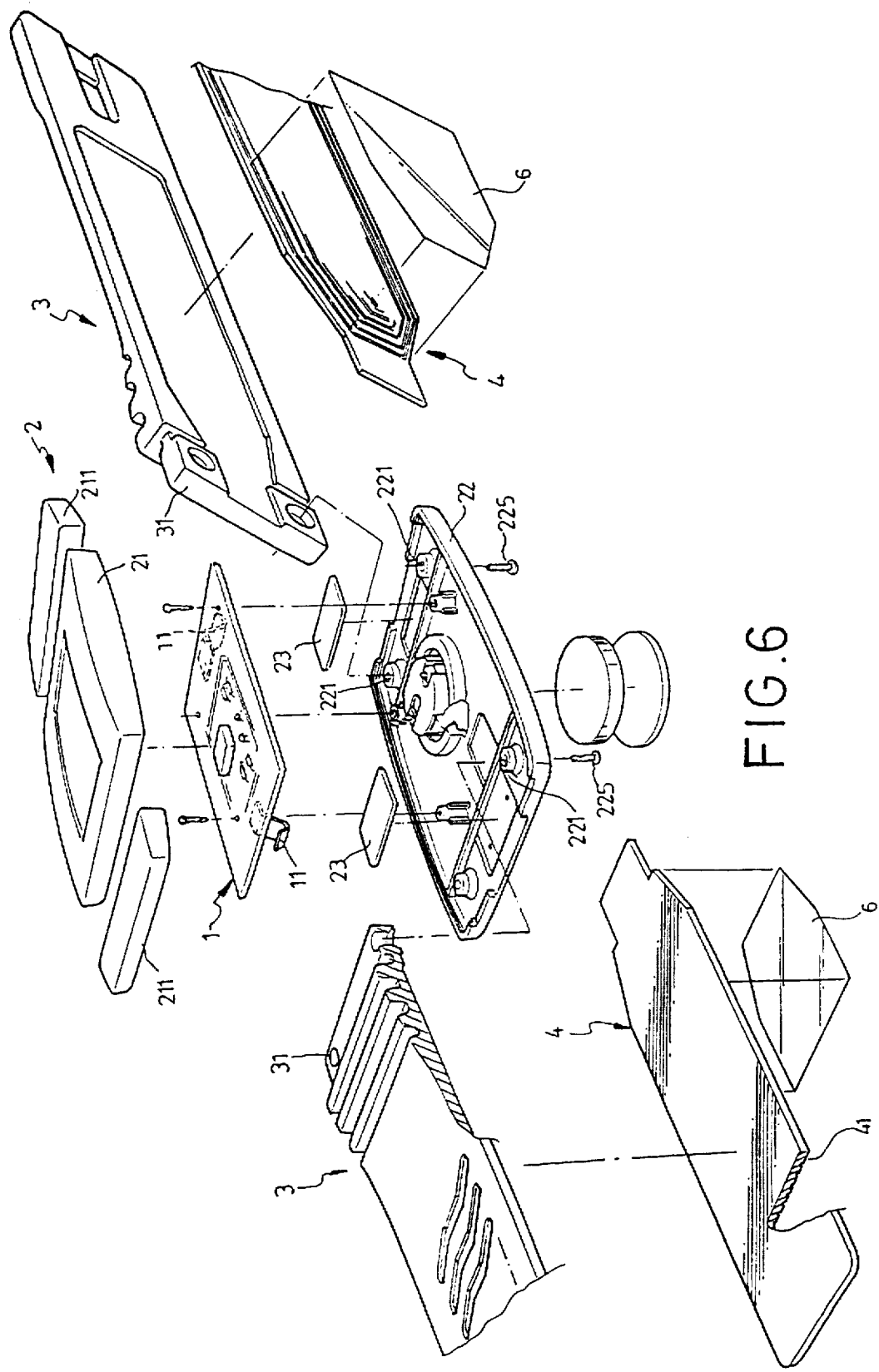
FIG. 6 is an exploded perspective view of the third embodiment made according to the present invention.
Figure 7:
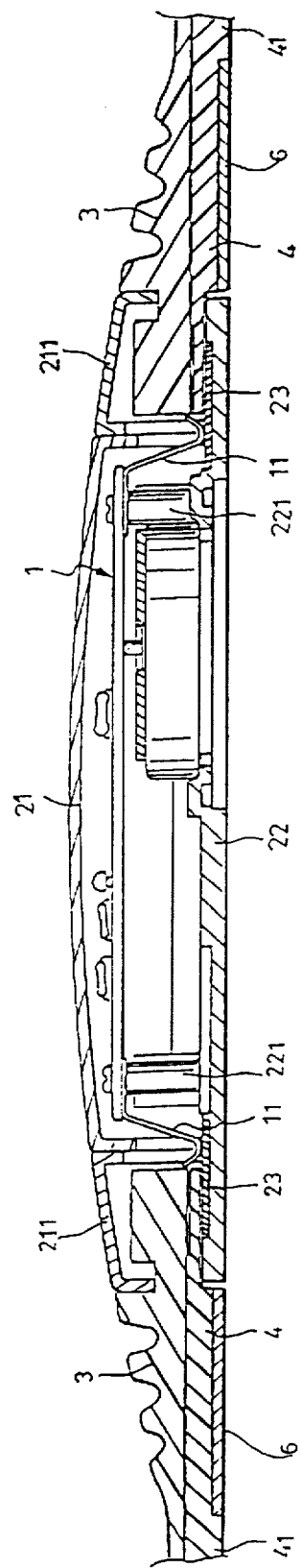
FIG. 7 is a cross sectional view of the heart beat transmitter shown in FIG. 6.

Now referring to FIGS. 6 and 7, an insulating layer 6 is disposed at the conductive rubber plate 4 in the area adjacent to the surface of the housing 2. This will reduce the noise interference which results from a larger contacting area. In this case, only the conductive portion 41 of the conductive rubber plate 4 is naked since the front portion is covered by the insulating layer.

When the user wears this heart beat transmitter, it only contacts with the chest of user on both sides, according the contacting area is reduced, the noise interference is reduced accordingly and the receiving performance is increased.

The installation of the insulating layer onto the conductive rubber plate 4 can be performed by "injecting" an insulating material thereof to replace the attachment of the insulating layer. While preferred embodiments of the invention have been disclosed in foregoing specification, it is understood by those skilled in the art that variations and modifications thereof can be made without departing from the spirit and scope of the invention, as set forth in the following claims.

I claim:

1. A heart beat transmitter to be worn by an user comprising:

a housing, a pair of metal plates within said housing, a pair of fastening straps secured to said housing, each of said fastening straps having an elongate conductive rubber plate in contact therewith, each of said conductive rubber plates contacting one of said metal plates in said housing, said conductive rubber plates detecting the heart rate of the user, a circuit board within said housing for decoding the signal received from said conductive rubber plates and transmitting a signal to a receiver, and conductive members connecting said circuit board with each of said metal plates within said housing and establishing an electrical connection therebetween.

2. The heart beat transmitter as defined in claim 1, wherein said conductive members are conductive rubber posts.

3. The heart beat transmitter as defined in claim 1, wherein said conductive members are conductive wires.

4. The heart beat transmitter as defined in claim 1, wherein said conductive members are conductive spring plates.

5. The heart beat transmitter as defined in claim 4, wherein each of said conductive spring plates have one end attached to said circuit board and a second end extending to and in contact with one of said metal plates.

6. The heart beat transmitter as defined in claim 5, wherein said second end of each of said conductive spring plates has a V-shape and contacts one of said metal plates with a tip of said V-shape end.

7. The heart beat transmitter as defined in claim 1, wherein each of said fastening straps has a cavity for placing one of said conductive rubber plates therein.

8. The heart beat transmitter as defined in claim 1, wherein said housing comprises an upper case and a lower case attached to said upper case, and said circuit board is attached to said lower case.

9. The heart beat transmitter as defined in claim 8, wherein each of said fastening straps has a fastening portion attached to said lower case.

10. A heart beat transmitter to be worn by an user comprising:

a housing, a pair of metal plates within said housing, a pair of fastening straps secured to said housing, each of said fastening straps having an elongate conductive rubber plate in contact therewith, each of said conductive rubber plates contacting one of said metal plates in said housing, each of said conductive rubber plates having an insulating layer in an area adjacent to said housing to reduce a contacting area with the user, said conductive rubber plates detecting the heart rate of the user, a circuit board within said housing for decoding the signal received from said conductive rubber plates and transmitting a signal to a receiver, and conductive members connecting said circuit board with each of said metal plates within said housing and establishing an electrical connection therebetween.

11. The heart beat transmitter as defined in claim 10, wherein said conductive members are conductive rubber posts.

12. The heart beat transmitter as defined in claim 10, wherein said conductive members are conductive wires.

13. The heart beat transmitter as defined in claim 10, wherein said conductive members are conductive spring plates.

14. The heart beat transmitter as defined in claim 13, wherein each of said conductive spring plates have one end attached to said circuit board and a second end extending to and in contact with one of said metal plates.

15. The heart beat transmitter as defined in claim 14, wherein said second end of each of said conductive spring plates has a V-shape and contacts one of said metal plates with a tip of said V-shape end.

16. The heart beat transmitter as defined in claim 10, wherein each of said fastening straps has a cavity for placing one of said conductive rubber plate.

17. The heart beat transmitter as defined in claim 10, wherein said housing comprises an upper case and a lower case attached to said upper case, and said circuit board is attached to said lower case.

18. The heart beat transmitter as defined in claim 17, wherein each of said fastening straps has a fastening portion attached to said lower case.

* * * * *